United States Patent [19]

Niira, deceased et al.

[11] Patent Number: 4,938,955

[45] Date of Patent: * Jul. 3, 1990

[54] ANTIBIOTIC RESIN COMPOSITION

[75] Inventors: Reiji Niira, deceased, late of Kokubunji, by Yuriko Niira, Kiyotaka Niira, Hideaki Niira, heirs; Tatuo Yamamoto, Inazawa; Masashi Uchida; Yoshihiro Fukuoka, both of Nagoya, all of Japan

[73] Assignees: Shingawa Fuel Co., Ltd; Shinanen New Ceramic Corporation, both of Japan

[*] Notice: The portion of the term of this patent subsequent to Jul. 3, 2007 has been disclaimed.

[21] Appl. No.: 183,000

[22] Filed: Apr. 18, 1988

[30] Foreign Application Priority Data

Apr. 22, 1987 [JP] Japan .................................. 62-99219

[51] Int. Cl.$^5$ ..................... A61K 31/74; A01N 59/16; A01N 59/20; A01N 59/00

[52] U.S. Cl. ..................................... 424/79; 424/618; 424/630; 424/641; 424/688; 424/617; 424/719; 523/122; 521/25; 521/63; 524/450

[58] Field of Search ................. 424/79, 132, 618, 140, 424/630, 145, 641, 157, 688, 131, 617, 166, 719; 523/122; 521/25, 63; 524/450

[56] References Cited

U.S. PATENT DOCUMENTS

| | | | |
|---|---|---|---|
| 4,000,100 | 12/1976 | Baldyga | 524/147 |
| 4,250,081 | 2/1981 | Bode et al. | 524/450 |
| 4,525,410 | 6/1985 | Hagwara | 424/131 |

FOREIGN PATENT DOCUMENTS

| | | |
|---|---|---|
| 23546 | 1/1984 | Australia . |
| 61818 | 8/1986 | Australia . |
| 13-4422 | 10/1938 | Japan . |
| 52-92000 | 8/1977 | Japan . |
| 78112660 | 9/1978 | Japan . |
| 55-38358 | 3/1980 | Japan . |
| 55-164236 | 12/1980 | Japan . |
| 57-77022 | 5/1982 | Japan . |
| 59-37956 | 3/1984 | Japan . |
| 59-133235 | 7/1984 | Japan . |
| 60-64611 | 4/1985 | Japan . |
| 60-79433 | 6/1985 | Japan . |
| 60-100504 | 6/1985 | Japan . |
| 60-136795 | 9/1985 | Japan . |
| 60-136796 | 9/1985 | Japan . |
| 60-174707 | 9/1985 | Japan . |
| 60-178810 | 9/1985 | Japan . |
| 60-181002 | 9/1985 | Japan . |
| 60-181370 | 9/1985 | Japan . |
| 60-184325 | 9/1985 | Japan . |
| 60-202162 | 10/1985 | Japan . |
| 61-137564 | 6/1986 | Japan . |
| 61-138647 | 6/1986 | Japan . |
| 61-138658 | 6/1986 | Japan . |
| 61-138795 | 6/1986 | Japan . |
| 61-103401 | 7/1986 | Japan . |
| 61-232253 | 10/1986 | Japan . |
| 61-232253 | 10/1986 | Japan . |
| 62-7746 | 1/1987 | Japan . |
| 62-7747 | 1/1987 | Japan . |
| 62-7748 | 1/1987 | Japan . |
| 62-70221 | 3/1987 | Japan . |
| 62-195037 | 8/1987 | Japan . |
| 62-195038 | 8/1987 | Japan . |
| 62-41775 | 9/1987 | Japan . |
| 62-238900 | 10/1987 | Japan . |
| 62-241932 | 10/1987 | Japan . |
| 62-241939 | 10/1987 | Japan . |
| 62-243665 | 10/1987 | Japan . |

OTHER PUBLICATIONS

Donald W. Breck, Structure, Chemistry, And Use, John Wiley & Sons, New York, 1964, pp. 19-27.
Daniel S. Barker, The American Mineralogist, vol. 49, 1964, pp. 851-857.
Richard C. Erd et al, The American Mineralogist, vol. 49, 1964, pp. 831-850.

Primary Examiner—Joseph L. Schofer
Assistant Examiner—Carmen B. Pili-Curtis
Attorney, Agent, or Firm—Jacobs & Jacobs

[57] ABSTRACT

An antibiotic resin composition comprises at least one antibiotic zeolite of which ion-exchangeable ions are partially or completely replaced with ammonium ion-sand antibiotic metal ions, at least one discoloration inhibitor and at least one resin. The antibiotic resin composition exhibits excellent antibiotic property and does not discolor with time. Thus, the resin composition can be employed to form a variety of products which require antibacterial and/or antifungus properties.

12 Claims, 3 Drawing Sheets

ANTIBIOTIC RESIN COMPOSITION

BACKGROUND OF THE INVENTION

1. Field of the Invention

The present invention relates to an antibiotic resin composition and more particularly to an antibiotic resin composition which comprises antibiotic zeolites and does not discolor with time.

2. Description of the Prior Art

Heretofore, there have been known such inorganic antibiotics as silver-supporting active carbon as disclosed in Japanese Patent Un-examined Publication (hereinafter referred to as "J.P. KOKAI") No. 49-61950 and such organic antibacterial or antifungus agents as N-(fluorodichloromethylthio)-phthalimide. However, in the former (inorganic antibiotics), silver ions rapidly leach out therefrom and, therefore, it is difficult to attain a sustained antibiotic effect.

On the other hand, some of the latter (organic antibacterial or antifungus agents) have no antibacterial effect on certian kinds of bacteria and molds (in other words, they are inferior in general-purpose utility with respect to bacteria and molds). Further, even those having heat resistance sometimes decompose at a temperature of 150 to 300° C. This leads to reduction of antibacterial effect.

For the purpose of eliminating the aforementioned drawbacks associated with these conventional antibiotics, there have been developed so-called antibiotic zeolites which comprise an antibiotic component supported on zeolite, as disclosed in Japanese Patent Published for Opposition (hereunder referred to as "J.P. KOKOKU") No. 61-22977 and J.P. KOKAI No. 60-181002. Moreover, J.P. KOKAI No. 59-133235 discloses that such antibiotic zeolites are incorporated into a variety of resins to impart antibiotic properties thereto and the resultant resins can be widely used by forming them into antibiotic films, fibers, containers and the like.

However, such an antibiotic zeolite suffers from the disadvantage that it gradually discolors in the course of time. While this discoloration has no influence on the antibiotic effect of the antibiotic zeolite, products made using a resin in which such an antibiotic zeolite is incorporated sometimes discolor and this may, depending on the nature of the products, greatly reduce their commercial value.

SUMMARY OF THE INVENTION

Accordingly, an object of the present invention is to provide an antibiotic resin composition which does not discolor with time and which exhibits excellent antibiotic effect as high as that of the conventional resin compositions containing antibiotic zeolites.

Other objects of the present invention will be apparent from the following detailed explanation of the invention.

The aforementioned objects of the invention can effectively be accomplished by providing an antibiotic resin composition comprising at least one antibiotic zeolite of which ion-exchangeable ions are partially or completely replaced with ammonium ions and antibiotic metal ions, at least one discoloration inhibitor and at least one resin.

DESCRIPTION OF THE PREFERRED EMBODIMENT

Figure 1:
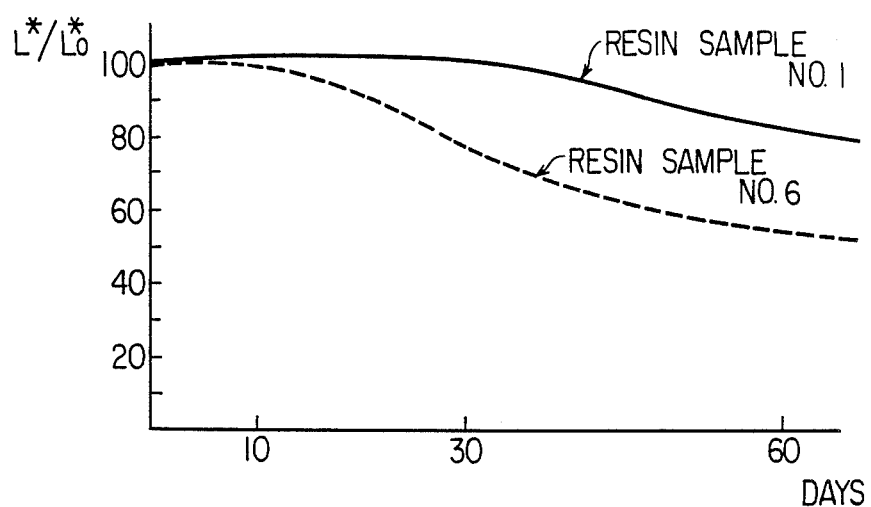
FIGS. 1 to 5 are diagrams illustrating color change of Samples of resins, into which antibiotic zeolites were incorporated by kneading, plotted against time.

The present invention will hereunder be explained in more detail.

In the antibiotic resin composition of the present invention, either natural zeolites or synthetic zeolites may be used as the "zeolite component". Zeolite is in general aluminosilicate having a three dimensional skeletal structure and represented by the general formula: $XM_{2/n}O\text{-}Al_2O_3\text{-}YSiO_2\text{-}ZH_2O$. In the general formula, M represents an ion-exchangeable ion and in general a monovalent or divalent metal ion, n represents atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. However, the preasent invention is not restricted to these specific examples. The ion-exchange capacities of these exemplified zeolites are as follows: A-type zeolite =7 meq./g; X-type zeolite =6.4 meq./g; Y-type zeolite =5 meq./g; T-type zeolite =3.4 meq./g; sodalite =11.5 meq./g; mordenite =2.6 meq./g; analcite =5 meq./g; clinoptilolite =2.6 meq./g; chabazite =5 meq./g; and erionite =3.8 meq./g. Thus, all the zeolites listed above have ion-exchange capacity sufficient to undergo ion-exchange with ammonium and antibiotic metal ions and these zeolites may be used alone or in combination, in the resin composition.

In the antibiotic zeolites used in the present invention, ion-exchangeable ions present in zeolite, such as sodium ions, calcium ions, potassium ions, magnesium ions and iron ions are completely or partially replaced with ammonium and antibiotic metal ions.

The content of ammonium ions in zeolite is desirably 0.5 to 5%, preferably 0.5 to 2% in view of effectively preventing the discoloration of the zeolite.

Examples of the antibiotic metal ions include ions of silver, copper, zinc, mercury, tin, lead, bismuth, cadmium, chromium and thallium. Preferably the antibiotic metal ions are silver, copper and zinc. These ions may be used alone or in combination. From the viewpoint of the antibiotic effect, in general the antibiotic metal ions are contained in the zeolite in an amount preferably ranging from 0.1 15% of the zeolite. In the present invention, the content of silver ions in the zeolite is 0.1 to 15%, preferably 0.1 to 5%; that of copper ions is preferably 0.1 to 8%; and that of zinc ions is preferably 0.1 to 8%, from the viewpoint of imparting effective antibiotic properties to the zeolite. In this connection, the term "%" herein means "% by weight" on the basis of the weight of the zeolite weighed after drying at 110° C.

In the present invention, it is particularly preferred to use antibiotic zeolites of which ion-exchangeable ions are completely or partially replaced with ammonium and silver ions and further either or both of copper and zinc ions.

Methods for preparing the antibiotic zeolite used in the invention will now be explained below.

The antibiotic zeolite as the zeolite component of the antibiotic resin composition of the invention may be obtained by bringing a zeolite into contact with a previously prepared aqueous mixed solution containing ammonium ions and antibiotic metal ions such as silver, copper and zinc ions to cause ion-exchange between ion-exchangeable ions in the zeolite and the aforesaid ions. The contact between these ions may be carried out according to a batchtechnique or a continuous technique (such as a column method) at a temperature of from 10° to 70° C., preferably 40° to 60° C., for 3 to 24 hours, preferably 10 to 24 hours. During the contact, the pH value of the aqueous mixed solution is adjusted to 3 to 10, preferably 5 to 7 in view of preventing the silver oxide and the like from causing deposition on the surface of the zeolite or within the pores thereof. In addition, each of the ion species is generally used in the form of a salt to prepare the aqueous mixed solution. For instance, there may be mentioned such an ammonium ion source as ammonium nitrate, ammonium sulfate and ammonium acetate; such a silver ion source as silver nitrate, silver sulfate, silver perchlorate, silver acetate and diamine silver nitrate; such a copper ion source as copper(II) nitrate, copper sulfate, copper perchlorate, copper acetate and tetracyan copper potassium; such a zinc ion source as zinc(II) nitrate, zinc perchlorate, zinc acetate and zinc thiocyanate; such a mercury ion source as mercury perchlorate, mercury nitrate and mercury acetate; such a tin ion source as tin sulfate; such a lead ion source as lead sulfate and lead nitrate; such a bismuth ion source as bismuth chloride and bismuth iodide; such a cadmium ion source as cadmium perchlorate, cadmium sulfate, cadmium nitrate and cadmium acetate; such a chromium ion source as chromium perchlorate, chromium sulfate, chromium ammonium sulfate and chromium acetate; and such a thallium ion source as thallium perchlorate, thallium sulfate, thallium nitrate and thallium acetate.

The content of the ions such as ammonium ions in the zeolite may properly be controlled by adjusting the concentration of each ion species (or salt) in the aforesaid aqueous mixed solution. For instance, if the antibiotic zeolite comprises ammonium and silver ions, the antibiotic zeolite having an ammonium ion content of 0.5 to 5% and a silver ion content of 0.1 to 5% can properly be obtained by bringing a zeolite into contact with an aqueous mixed solution having an ammonium ion concentration of 0.85 to 3.1 mole/l and a silver ion concentration of 0.002 to 0.15 mole/l. Moreover, if the antibiotic zeolite further comprises copper and zinc ions, the antibiotic zeolite having a copper ion content of 0.1 to 8% and a zinc ion content of 0.1 to 8% can properly be prepared by employing an aqueous mixed solution containing 0.1 to 0.85 mole/l of copper ions and 0.15 to 1.2 mole/l of zinc ions in addition to the aforementioned amount of ammonium and silver ions.

Alternatively, the antibiotic zeolite used herein may also be prepared by using separate aqueous solutions each containing a single different ion species (or salt) and bringing a zeolite into contact with the solutions one by one to cause ion-exchange therebetween. The concentration of each ion species in a specific solution can be determined in accordance with the concentrations of these ion species in the aforementioned aqueous mixed solution.

After completion of the ion-exchange, the zeolite thus treated is thoroughly washed with water followed by drying. The zeolite is preferably dried at a temperature of 105 to 115° C. under normal pressure or at a temperature of 70 to 90° C. under a reduced pressure (1to 30 torr).

After drying, the antibiotic zeolite thus prepared is pulverized and classified according to need and then is incorporated into a resin composition to form an antibiotic resin composition of the present invention.

The "anti-discoloring agent" as used herein may be any of compounds known as ultraviolet absorbers, antioxidants, light stabilizers, ultraviolet stabilizers, processing stabilizers, metal deactivators or fluorescent whiteners.

As such discoloration inhibitors it is possible to use at least one member selected from the group consisiting of, for instance, benzotriazole type compounds, oxalic acid anilide type compounds, salicylic acid type compounds, cyanoacrylate type compounds, benzophenone type compounds, hindered amine type compounds, hindered phenol type compounds, phosphorus type compounds, sulfur type compounds, and hydrazine type compounds.

Examples of the benzotriazole type compounds are 2-(5-methy-2-hydroxyphenyl)-benzotriazole, 2-(2-hydroxy-3,5-bis (alpha,alpha-dimethylbenzyl)-phenyl)-2H-benzotriazole, 2-(3,5-di-tert-butyl-2-hydroxyphenyl)-benzotriazole, 2-(3-tert-butyl-5-methyl-2-hydroxyphenyl)-5-chloroenzotriazole, 2-(3,5-di-tert-butyl-2-hydroxyphenyl)-5-chlorobenzotriazole and 2-(3,5-di-tert-amyl-2-hydroxyphenyl)-benzotriazole.

Examples of the oxalic acid anilide type compounds are 2-ethoxy-2'-ethyloxalic acid bisanilide and 2-ethoxy-5-tert-butyl-2'-ethyloxalic acid bisanilide.

Examples of the salicylic acid type compounds are phenyl salicylate, p-tert-butylphenyl salicylate and p-octylphenyl salicylate.

Examples of the cyanoacrylate type compounds include 2-ethylhexyl-2-cyano-3,3'-diphenyl acrylate and ethyl-2-cyano-3,3'-diphenyl acrylate.

As the benzophenone type compounds, there may be mentioned, for instance, 2,4-dihydroxybenzophenone, 2-hydroxy-4-methoxybenzophenone, 2-hydroxy -4octoxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methyoxy-5-sulfobenzophenone.

Examples of the hindered amine type compounds are dimethyl succinate/1-(2-hydroxyethyl)-4-hydroxy-2,2,6,6-tetramethylpiperidinepolycondensate, poly((6-(1,1,3,3-tetramethylbutyl)-imino-1,3,5-triazine-2,4-diyl) ((2,2,6,6-tetramethyl-4-piperidyl)-imino)-hexamethylene-((2,2,6,6-tetramethyl-4-piperidyl)-imino)), and bis(1,2,2,6,6-pentamethyl-4-piperidyl) 2-(3,5-di-tert-butyl-4-hydroxybenzyl)-2-n-butylmalonate.

Examples of the hindered phenol type compounds include triethylene glycol bis(3-(3-tert-butyl-5-methyl-4-hydroxyphenyl)-propionate), 1,6-hexanediol bis(3-(3,5-ditert-butyl-4-hydroxyphenyl)-propionate), 2,4-bis(n-octylthio)-6-(4-hydroxy-3,5-di-tert-butylanilino)-1,3,5-triazine, pentaerythritol tetrakis(3-(3,5-di-tert-butyl-4-hydroxyphenyl)-propionate), 2,2-thiodiethylene-bis(3-(3,5-di-tert-butyl-4-hydroxyphenyl)-propionate), octadecyl 3-(3,5-tert-butyl-4-hydroxyphenyl)-propionate, 2,2-thiobis (4-methyl-6-tert-butylphenol), N,N'-hexamethylene-bis (3,5-di-tert-butyl-4-hydroxyhydrocinnamamide), 3,5-di-tert-butyl-4-hydroxy-benzylphosphonate diethyl ester, 1,3,5-trimethyl-2,4,6-tris (3,5-di-tert-butyl-4-hydroxybenzyl)benzene, calcium (ethyl bis(3,5-di-tert-butyl-4-hydroxybenzyl-phosphonate)) and tris-(3,5-di-tert-butyl-4hydroxybenzyl) isocyanurate.

Examples the of phosphorus type compounds are triphenyl phosphite, tris(nonylphenyl) phosphite, tris(2-ethylhexyl) phosphite, tridecyl phosphite, tris(tridecyl) phosphite, diphenyl mono(2-ethylhexyl) phosphite, diphenyl monodecyl phosphite, diphenyl monotridecyl phosphite, tetraphenyl tetra(tridecyl)-pentaerythritol tetraphosphite, tetra(tridecyl)-4,4'-isopropylidene diphenylphosphite, bis(tridecyl)-pentaerythritol diphosphite, distearylpentaerythritol diphosphite and tris(2,4-di-tertbutylphenyl) phosphite.

Examples of the sulfur type compounds are dilaurylthio dipropionate, dimyristylthio dipropionate and distearylthio dipropionate.

Examples of the hydradine type compounds include N,N'-bis (3-(3,5-di-tert-butyl-4-hydroxyphenyl)-propionyl)-hydradine.

These discoloration inhibitors may be used alone or in combination, in the resin composition of this invention.

The "resins" herein used may be natural, semisynthetic or synthetic resins which may be either thermoplastic or thermosetting resins. Typical examples thereof are polyethylene, polypropylene, vinyl chloride resins, ABS resins, polyesters, polyvinylidene chloride, polyamides, polystyrene, polyacetals, polyvinyl alcohols, polycarbonates, acrylic resins, fluorine plastics, polyurethane elastomer, polyester elastomer, phenolic resins, urea resins, melamine resins, unsaturated polyester resins, epoxy resins, urethane resins, rayon, cuprammonium rayons, acetate resins, natural rubbers, synthetic rubbers and EVA resins. These resins may be used alone or in combination.

The antibiotic resin composition of this invention may be obtained by admixing the aforementioned antibiotic zeolites, discoloration inhibitors and resins in a conventional manner and then be formed into a variety of products having various forms or shapes such as films, fibers, plates, containers and particulate materials.

The antibiotic zeolites are desirably incorporated into the resin composition in an amount of 0.1 to 50% and preferably 0.1 to 2%. For instance, in the case of a master batch, they are preferably used in an amount of 10 to 30% on the basis of the weight of the composition.

On the other hand, the amount of the discoloration inhibitors desirably ranges from 0.001 to 1.0% with respect to the weight of the resins used.

The antibiotic resin compositions according to the present invention exhibit excellent antibiotic properties. The antibiotic properties may be estimated by the assay of antibiotic action with respect to a variety of general bacteria, eumycetes and yeast.

In such an assay, the bacteria listed below may be employed:

*Bacillus cereus var mycoides*, ATCC 11778;
*Escherichia coli*, IFO 3301;
*Pseudomonas aeruginosa*, IIDP-1;
*Staphylococcus aureus*, ATCC 6538P;
*Streptococcus faecalis*, RATCC 8043;
*Aspergillus niger*, IFO 4407;
*Aureobasidium pullulans*, IFO 6353;
*Chaetomium globosum*, ATCC 6205;
*Gliocladium virens*, IFO 6355;
*Penicillum funiculosum*, IFO 6345;
*Candida albicans*, IFO 1594; and
*Saccharomyces cerevisiae*, IFO 1950.

The antibiotic property is estimated by introducing test Samples of antibiotic resin composition into an Erlenmeyer flask containing sterilized physiological saline, shaking at room temperature and periodically determining the viable cell count in the solution to be tested.

As explained above in detail, the antibiotic resin composition of the present invention exhibits excellent antibiotic property and suffers almost no discoloration. Therefore, the resin composition can effectively be adopted to form a variety of products which can suppress the proliferation of bacteria and/or molds.

the antibiotic resin compositions of the present invention will hereunder be explained in more detail with reference to the following non-limitative Examples and Reference Examples. In addition, the effect practically achieved by the present invention will also discussed in comparison with Comparative Examples.

REFERENCE EXAMPLE (PREPARATION OF ANTIBIOTIC ZEOLITE)

In this Reference Example, the following two types of zeolites were used: A-type zeolite ($Na_2O$-$Al_2O_3$-$1.9SiO_2$-$XH_2O$; average particle size = 1.5 microns) and Y-type zeolite ($1.1Na_2O$-$Al_2O_3$-$4SiO_2$-$XH_2O$; average particle size 0.7 microns). As the source of the ion species required for ion-exchange, four kinds of salts: $NH_4NO_3$, $AgNO_3$, $Cu(NO_3)_2$ and $Zn(NO_3)_2$ were used.

Table I shows the details of the kinds of zeolites, the kinds of salts and their concentrations in an aqueous mixed solution used to prepare Samples. Thus, nine Samples of antibiotic zeolites were obtained.

Each Sample was prepared as follows: 1 kg of the zeolite which had been dried under heating at 110° C. was added to water to form 1.3 liters of slurry, then the slurry was stirred to degassify it, an appropriate amount of 0.5 N nitric acid solution and water were added thereto to adjust the pH to 5 to 7 and to thus obtain a slurry of a total volume of 1.8 liters. Thereafter, ion-exchange was carried out by adding, to the slurry, 3 liters of a mixed aqueous solution containing desired salts each present in a desired amount to obtain a slurry having a total volume of 4.8 liters and maintaining the slurry at a temperature of 40 to 60° C. for 10 to 24 hours while stirring to hold the slurry at an equilibrium state. After the ion-exchange was finished, the zeolite phase was filtered off followed by washing with water at room temperature or warm water until almost no excess silver, copper or zinc ions remained in the zeolite phase. Then, Samples thus prepared were dried under heating at 110° C. and thus nine Samples of the antibiotic zeolites were obtained. The data observed on these antibiotic zeolite Samples No.1 to No. 9 are summarized in Table I.

TABLE I

| Sample No. | Kind of zeolite | Content in the zeolite (%) | | | | Yield (g) |
|---|---|---|---|---|---|---|
| | | NH₄ | Ag | Cu | Zn | |
| 1 | A | 1.3 | 2.9 | — | 5.4 | 990 |
| 2 | Y | 0.8 | 2.6 | 4.9 | — | 945 |
| 3 | A | 1.3 | 3.1 | 5.6 | — | 985 |
| 4 | A | 2.4 | 2.3 | 8.3 | — | 990 |
| 5 | A | 1.3 | 2.0 | 8.0 | — | 982 |

TABLE I-continued

| 6 | A | 2.5 | 2.1 | — | 5.4 | 990 |
| 7 | A | 1.2 | 3.0 | — | 10 | 975 |
| 8 | A | 1.0 | 5.0 | 10.5 | — | 975 |
| 9 | A | 1.5 | 3.2 | 8 | — | 990 |

| Sample No. | Composition of mixed aq. soln. (M/l) | | | | pH of slurry | Ion-Ex. time (hr.) |
|---|---|---|---|---|---|---|
| | $NH_4NO_3$ | $AgNO_3$ | $Cu(NO_3)_2$ | $Zn(NO_3)_2$ | | |
| 1 | 0.5 | 0.09 | — | 0.35 | 6.2 | 15 |
| 2 | 0.3 | 0.08 | 0.30 | — | 6.5 | 15 |
| 3 | 0.5 | 0.10 | 0.35 | — | 6.2 | 15 |
| 4 | 0.7 | 0.07 | 1.00 | — | 5.1 | 15 |
| 5 | 0.7 | 0.06 | 0.70 | — | 5.4 | 15 |
| 6 | 0.7 | 0.07 | — | 0.40 | 5.8 | 15 |
| 7 | 0.8 | 0.10 | — | 1.20 | 4.7 | 15 |
| 8 | 0.9 | 0.15 | 1.50 | — | 4.8 | 15 |
| 9 | 0.7 | 0.10 | 0.80 | — | 5.1 | 15 |

EXAMPLE 1 (PREPARATION OF ANTIBIOTIC RESIN COMPOSITION)

Antibiotic resin compositions were prepared as follows:

The antibiotic zeolite prepared in Reference Example was maintained at 200° C. for 3 hours to dry it. After kneading 1 part by weight of the heat dried antibiotic zeolite and 0.5 parts by weight of a discoloration inhibitor into 100 parts by weight of resin the resultant resin composition was injection molded (residence time=2 minutes) into Samples (size of the pieces: 7.3 cm ×4.4 cm×2 mm). The kinds of the antibiotic zeolites, the discoloration inhibitors and resins used are listed in Table II.

EXAMPLE 2 (TEST OF DISCOLORATION)

Figure 2:
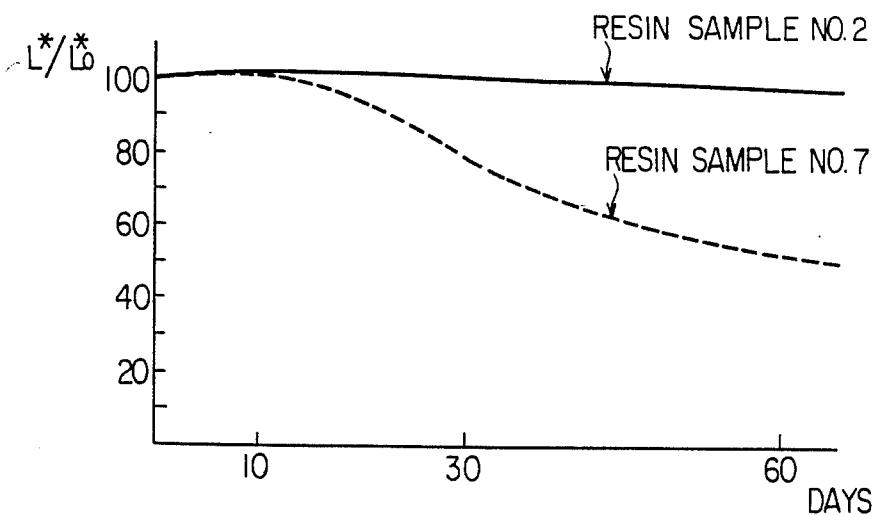
Figure 3:
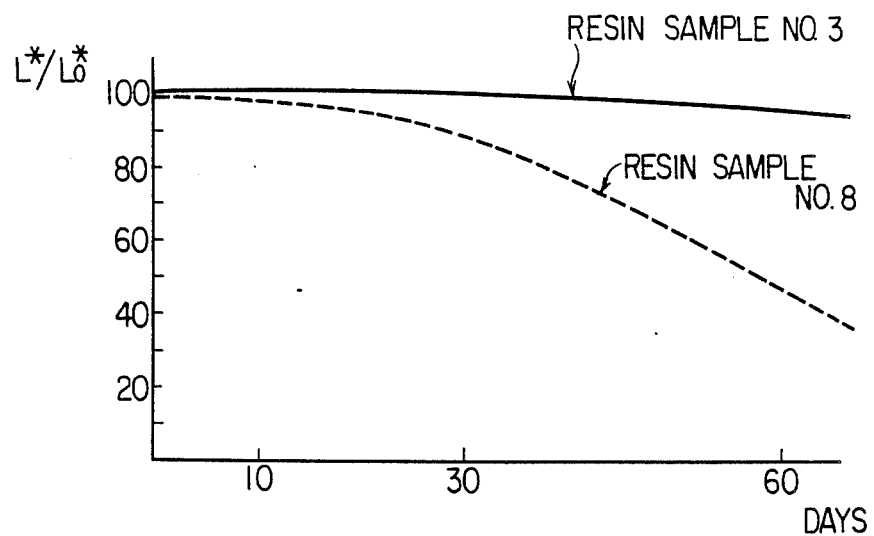
Figure 4:
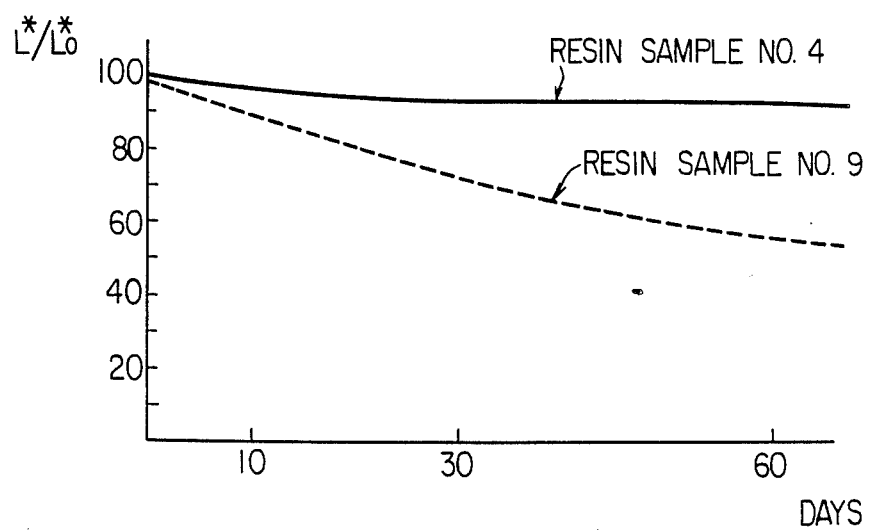
Figure 5:
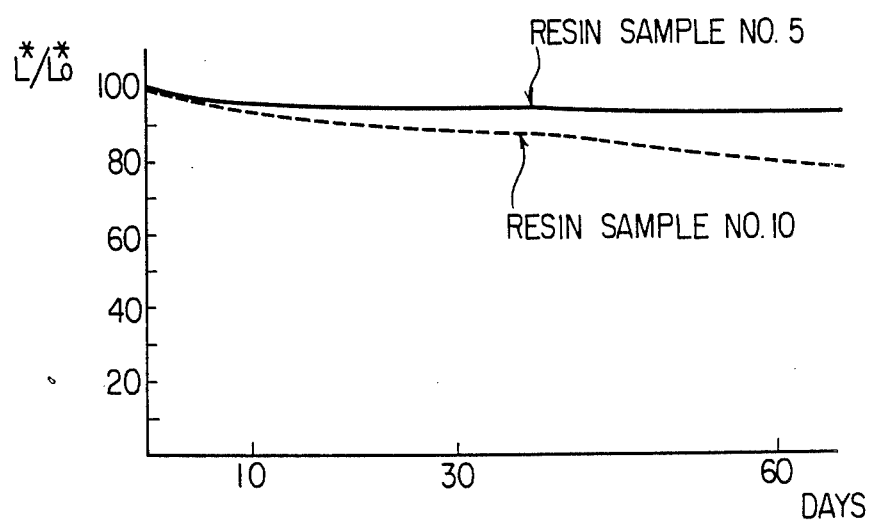

The resin Samples No.1 to No. 5 prepared in Example 1 were irradiated with sun light in the air. The color of the Samples was determined by placing each Sample on a white Kent paper (L*a*b* 93.1; −0.7; −0.5) with a CR-100 Minolta color-color difference meter (using $D_{65}$ rays). The results obtained are expressed in accordance with L*a*b* colorimetric system (CIE 1976). In addition, the results on L* are shown in the attached FIGS. 1 to 5.

COMPARATIVE EXAMPLE

The same procedures as in Example 1 were repeated except that no discoloration inhibitors were used in forming resin Samples No. 6 to No. 10 (see Table II) similar to those No. 1 to No. 5. The test on discoloration of Example 1 was carried out on the resultant Samples. The results obtained are shown in FIGS. 1 to 5.

TABLE II

| Resin Sample No. | Antibiotic zeolite No. | Anti-discoloring agent No. | Resin used |
|---|---|---|---|
| 1 | 1 | 1 | polystyrene |
| 2 | 1 | 2 | polystyrene |
| 3 | 2 | 3 | nylon |
| 4 | 2 | 4 | nylon |
| 5 | 3 | 5 | LDPE |
| 6 | 1 | — | polystyrene |
| 7 | 1 | — | polystyrene |
| 8 | 2 | — | nylon |
| 9 | 2 | — | nylon |
| 10 | 3 | — | LDPE |

(Discoloration Inhibitors Used)
No. 1: Poly((6-(1,1,3,3-tetramethylbutyl)-imino-1,3,5-triazine-2,4-diyl)((2,2,6,6-tetramethyl-4-piperidyl)-imino)-hexamethylene-((2,2,6,6-tetramethyl-4-piperidyl)-imino));
No. 2: 2-(3,5-di-tert-amyl-2-hydroxyphenyl)-benzotriazole;
No. 3: Octadecyl 3-(3,5-di-tert-butyl-4-hydroxyphenyl)-propionate;
No. 4: Dimethyl succinate/1-(2-hydroxyethyl)-4-hydroxy-2,2,6,6-tetramethylpiperidine polycondensate;
No. 5: N,N'-bis(3-(3,5-di-tert-butyl-4-hydroxyphenyl)-propionyl)-hydrazine.
(Resins Used)
Polystyrene: HH-102 (available from MITSUBISHI MONSANT CO., LTD.)
Nylon: Novamid 1010J (available from MITSUBISHI CHEMICAL INDUSTRIES, LTD.)
LDPE: Petrocene 207 (available from TOYO SODA MANUFACTURING CO., LTD.)

EXAMPLE 3 (ASSAY OF ANTIBIOTIC PROPERTY)

The antibiotic property of the antibiotic resin composition was determined utilizing the following strains:
Strains Used
(1) *Escherichia coli,* IFO 3301
(2) *Staphylococcus aureus,* IFO 13276
(3) *Pseudomonas aeruginosa,* IID P-1
(4) *Bacillus cereus var. mycoides,* ATCC 11778
(5) *Streptococcus faecalis* R, ATCC 8043
(6) *Candida albicans,* IFO 1594
(7) *Saccharomyces cerevisiae,* IFO 1590
(8) *Vibrio parahaemolyticus,* IFO 12711

Four sheets of resin Samples shown in Table IV (1 g each) were introduced into a 300 ml Erlenmeyer flask containing 40 ml of sterilized saline and a diluted bacteria solution was added thereto so that the number of bacteria was about $10^4$/ml. In this respect, the diluted bacteria solutions were prepared by culturing the strain (1) to (5) or (8) (bacteria) in a common broth or a heart infusion broth at 35° C. for 16 to 20 hours and then properly diluting the culture with sterilized saline or by culturing the test strain (6) or (7) (yeast) in a YM broth at 25° C. for 1 to 2 days and then properly diluting the culture with sterilized saline. The flask was shaken at room temperature while periodically determining the viable cell count. The measurement was carried out at 0, 6, 24, and 48 hours after the introduction of the bacteria solution. The determination of the viable cell count was carried out after culturing the bacteria on SCDLP agar medium at 35° C. for 2 days or culturing the yeast on GPLP agar medium at 25° C. for 7 days. The results observed are summarized in Table III.

TABLE III

| Strain | Resin Sample | Viable cell count per 1 ml of culture Shaking time (hours) | | | |
|---|---|---|---|---|---|
| | | 0 | 6 | 24 | 48 |
| (1) | No. 1 | $1.8 \times 10^4$ | $6.5 \times 10^3$ | $4.1 \times 10^2$ | 0 |
| (1) | Control | $1.9 \times 10^4$ | $2.5 \times 10^3$ | $2.3 \times 10^2$ | $5.7 \times 10^2$ |
| (5) | No. 1 | $6.4 \times 10^4$ | 0 | 0 | 0 |
| (5) | Control | $9.0 \times 10^4$ | $7.1 \times 10^4$ | $6.3 \times 10^4$ | $7.3 \times 10^4$ |
| (3) | No. 2 | $3.5 \times 10^4$ | 0 | 0 | 0 |
| (3) | Control | $6.7 \times 10^4$ | $1.9 \times 10^4$ | $9.8 \times 10^2$ | $1.9 \times 10^2$ |
| (6) | No. 2 | $2.3 \times 10^4$ | $1.9 \times 10^2$ | 0 | 0 |
| (6) | Control | $3.6 \times 10^4$ | $4.2 \times 10^4$ | $3.0 \times 10^4$ | $2.0 \times 10^4$ |
| (7) | No. 2 | $8.8 \times 10^3$ | 0 | 0 | 0 |
| (7) | Control | $1.3 \times 10^4$ | $4.5 \times 10^3$ | $3.7 \times 10^3$ | $3.4 \times 10^3$ |
| (1) | No. 3 | $1.1 \times 10^4$ | $1.2 \times 10^3$ | 0 | 0 |
| (1) | Control | $5.7 \times 10^3$ | $5.6 \times 10^3$ | $3.6 \times 10^4$ | $3.2 \times 10^5$ |
| (3) | No. 3 | $3.4 \times 10^4$ | $4.1 \times 10^3$ | 0 | 0 |
| (3) | Control | $3.1 \times 10^4$ | $1.1 \times 10^4$ | $8.8 \times 10^2$ | $1.9 \times 10^2$ |
| (8) | No. 3 | $7.6 \times 10^3$ | $5.3 \times 10^3$ | $1.3 \times 10^2$ | 0 |
| (8) | Control | $1.5 \times 10^4$ | $1.5 \times 10^4$ | $5.0 \times 10^3$ | $1.5 \times 10^3$ |
| (1) | No. 4 | $5.5 \times 10^3$ | $3.6 \times 10^2$ | 0 | 0 |
| (1) | No. 5 | $6.4 \times 10^3$ | $2.5 \times 10$ | 0 | 0 |
| (1) | Control | $5.7 \times 10^3$ | $5.6 \times 10^3$ | $3.6 \times 10^4$ | $3.2 \times 10^5$ |
| (2) | No. 5 | $1.7 \times 10^4$ | $1.3 \times 10^3$ | $1.9 \times 10$ | 0 |
| (2) | Control | $1.8 \times 10^4$ | $3.1 \times 10^3$ | $5.6 \times 10^2$ | $3.2 \times 10^2$ |
| (3) | No. 4 | $1.7 \times 10^4$ | $2.8 \times 10^3$ | 0 | 0 |
| (3) | Control | $3.1 \times 10^4$ | $1.4 \times 10^3$ | $8.8 \times 10^2$ | $1.9 \times 10^2$ |

TABLE IV

| Resin Sample No. | Resin Used | | Antibiotic zeolite | | Discoloring inhibitor | |
|---|---|---|---|---|---|---|
| | Kind | Amount used | Sample No. | Amount added | No. | Amount added |
| 1 | ABS | 100 | 3 | 0.8 | 1 | 0.5 |
| 2 | PVC | 100 | 4 | 0.5 | 2 | 0.5 |
| 3 | LDPE | 100 | 5 | 0.5 | 3 | 0.5 |
| 4 | HDPE | 100 | 6 | 1 | 4 | 0.5 |
| 5 | PP | 100 | 7 | 1 | 5 | 0.5 |

*The "amount used" or "amount added" are expressed in part by weight.
(Resins)
ABS resin: GTR-10 (available from DENKI KAGAKU KOGYO KABUSHIKI KAISHA)
Polyvinyl chloride: B-3050F2 (60 parts of DOP is added; available from DENKI KAGAKU KOGYO KABUSHIKI KAISHA)
Lowdensitypolyethylene: Suntec F-1920 (available from Asahi Chemical Industry Co., Ltd.)
High density polyethylene: Suntec HDS-360 (available from Asahi Chemical Industry Co., Ltd.)
Polypropylene: J-109G (available from Ube Industries, Ltd.).
(Discoloration Inhibitors)
No. 1: Hindered amine type compound (available from Japan Chiba Geigy Co., Ltd. under the trade name of CHIMASSORB 944LD);
No. 2: Benzotriazole type compound (available from the same company under the trade name of TINUVIN 328);
No. 3: Hindered phenol type compound (available from the same company under the trade name of IRUGANOX 1076);
No. 4: Hindered amine type compound (available from the same company under the trade name of TINUVIN 622LD);
No. 5: Hydrazine type compound (available from the same company under the trade name of IRUGANOX MD1024).

EXAMPLE 4 (TEST ON RESISTANCE TO MOLD)

Test on resistance to mold was determined by the agar plate method.

A mixed spore suspension (0.1 mil) TM as measured on a potato dextrose agar plate medium (1/10 concentration; agar concentration =1.5%) followed by placing thereon a 30 mm×30 mm piece of the resin Sample (see Table VI) and uniformly spraying the mixed spore suspension (0.05 ml) thereon. Then, the agar plate medium was cultured at 28+2° C. and a humidity of about 95% for 4 weeks and after 2 and 4 weeks, the growth of hypha thereof on the surface of the resin piece was observed visually. The results obtained are listed in Table V.

The mixed spore suspension was prepared as follows: The following strains were separately cultured on a potato dextrose-agar slant culture medium until sufficient spores were formed and the resulting spores were separately dispersed in 0.005% sodium dioctyl sulfosuccinate solution to form single spore suspensions. Thereafter, equivalent volumes of all spore suspensions were mixed together to thereby form the intended mixed spore suspension.

Strains
*Aspergillus niger*, IFO 4407
*Penicillium citrinum*, IFO 7784
*Rhizopus nigricans* (Strain stored in the Laboratory)
*Cladosporium cladosporioides*, IFO 6348
*Chaetomium globosum*, ATCC 6205

TABLE V

| Resin Sample No. | Results of the Visual Observation* | |
|---|---|---|
| | 2 weeks after | 4 weeks after |
| 1 | 2 | 2 |
| 2 | 1 | 1 |
| 3 | 1 | 1 |

*The results of the visual observation were converted to numerical values in accordance with the following criteria:
0: No growth of mold;
1: Mold grew on not more than 10% of the surface area;
2: Mold grew on 10 to 30% of the surface area;
3: Mold grew on 30 to 60% of the surface area;
4: Mold grew on not less than 60% of the surface area.

TABLE VI

| Resin Sample No. | Resin | Antibiotic Zeolite No. 9 | Discoloration Inhibitor |
|---|---|---|---|
| 1 | 100 | — | — |
| 2 | 100 | 0.5 | + |
| 3 | 100 | 1 | + |

Resin: PVC (60 parts of DOP is added; available from DENKI KAGAKU KOGYO KABUSHIKI KAISHA under the trade name of B-3050F2)
Antibiotic Zeolite: A-type zeolite (Ag = 3.2%; Cu = 8.0%; NH4 = 1.5%)
Discoloration Inhibitor: Hindered amine type compound (available from Japan Chiba Geigy Co., Ltd. under the trade name of CHIMASSORB 944LD).

What is claimed is:

1. An antibiotic resin composition, comprising at least one antibiotic zeolite the ion-exchangeable ions of which are partially or completely replaced with ammonium ions and antibiotic metal ions comprising silver ions at least one discoloration inhibitor selected from the group consisting of benzotriazole compounds, oxalic acid anilide compounds, salicylic acid compounds, cyanoacrylate compounds, benzophenone compounds, hindered amine compounds, hindered phenol compounds, phosphorus compounds, sulfur compounds and hydrazine compounds and at least one resin, wherein the amount of said ammonium ions is from 0.5 to 15 wt % and the amount of said silver ions is from 0.1 to 15 wt %, based on the weight of said zeolite weighed after drying at 110° C., and the amount of said discoloration inhibitor is from 0.001 to 1.0%, based on the weight of said resin.

2. An antibiotic resin composition according to claim 1 wherein the antibiotic metal ions are silver ions or silver ions and ions of at least one metal selected from the group consisting of copper, zinc, mercury, tin, lead, bismuth, cadmium, chromium and thallium.

3. An antibiotic resin composition according to claim 2 wherein the antibiotic metal ions are silver ions or silver ions and at least one member selected from the group consisting of copper ions and zinc ions.

4. An antibiotic resin composition according to claim 1 wherein the antibiotic zeolite is present in an amount of 0.1 to 50% by weight based on the weight of the composition.

5. An antibiotic resin composition according to claim 4 wherein the amount of the antibiotic zeolite ranges from 0.1 to 2% by weight.

6. An antibiotic resin composition according to claim 1 wherein the zeolilte is a natural or synthetic zeolite.

7. An antibiotic resin composition according to claim 6 wherein the zeolite is at least one member selected from the group consisting of A-zeolites, X-zeolites, Y-zeolites, T-zeolites, high-silica zeolites, sodalite, mordenite, analcite, clinoptilolite, chabazite and erionite.

8. An antibiotic resin composition according to claim 1 wherein the antibiotic zeolite includes 0.5 to 2% by weight of ammonium ions.

9. An antibiotic resin composition according to claim 1 wherein the antibiotic zeolite further comprises 0.1 to 8% by weight of copper ions and/or 0.1 to 8% by weight of zinc ions.

10. An antibiotic resin composition according to claim 1 wherein the resin is a natural, semisynthetic or synthetic resin.

11. An antibiotic resin composition according to claim 10 wherein the resin is a thermoplastic resin or thermosetting resin.

12. An antibiotic resin composition according to claim 11 wherein the resin is at least one member selected from the group consisting of polyethylene, polypropylene, polyvinyl chloride, ABS resins, polyesters, polyvinylidene chloride, polyamides, polystyrene, polyacetals, polyvinyl alcohols, polycarbonates, acrylic resins, fluorine resins, polyurethane elastomer, polyester elastomer, phenolic resins, urea resins, melamine resins, unsaturated polyester resins, epoxy resins, urethane resins, rayons, cuprammonium rayons, acetate resins, natural rubbers, synthetic rubber, and EVA resins.

* * * * *